(12) United States Patent
Dapremont et al.

(10) Patent No.: US 6,444,854 B1
(45) Date of Patent: Sep. 3, 2002

(54) PROCESS FOR THE PRODUCTION OF ENANTIOMERICALLY PURE OR OPTICALLY ENRICHED SERTRALINE-TETRALONE USING CONTINUOUS CHROMATOGRAPHY

(75) Inventors: Oliver Dapremont, Folsom, CA (US); Fiona Geiser, Glenn Mills, PA (US); Tong Zhang, Strasbourg (FR); Subramanian S. Guhan, Niantic, CT (US); Robert M. Guinn, Mystic, CT (US); George J. Quallich, North Stonington, CT (US)

(73) Assignee: Chiral Technologies Europe, Illkirch Cedex (FR)

( * ) Notice: Subject to any disclaimer, the term of this patent is extended or adjusted under 35 U.S.C. 154(b) by 0 days.

(21) Appl. No.: 09/700,435

(22) PCT Filed: Apr. 27, 1999

(86) PCT No.: PCT/US99/09037

§ 371 (c)(1),
(2), (4) Date: May 1, 2001

(87) PCT Pub. No.: WO99/57089

PCT Pub. Date: Nov. 11, 1999

(51) Int. Cl.[7] ............................................... C07C 45/00

(52) U.S. Cl. ........................ 568/314; 568/315; 568/316; 568/321

(58) Field of Search ................................. 568/314, 315, 568/316, 321

(56) References Cited

U.S. PATENT DOCUMENTS

| 5,288,916 A | | 2/1994 | Lorenz et al. |
|---|---|---|---|
| 5,456,825 A | * | 10/1995 | Negawa et al. |
| 5,466,880 A | * | 11/1995 | Quallich |
| 5,630,943 A | * | 5/1997 | Grill |

FOREIGN PATENT DOCUMENTS

| EP | 0719749 A | 7/1996 |
|---|---|---|

* cited by examiner

Primary Examiner—Sreeni Padmanabhan
Assistant Examiner—Sikarl A. Witherspoon
(74) Attorney, Agent, or Firm—Ladas & Parry

(57) ABSTRACT

A process for the production of enantiomerically pure or optically enriched sertraline-tetralone from a mixture containing two enantiomers using continuous chuomatography. The chromatography comprises a liquid mobile phase comprising at least one polar solvent and a solid chiral stationary phase comprising a derivatized polysaccharide that is selected from amylosic, cellulosic, chitosan, xylan, curdlan, and inulan class of polysaccharide.

21 Claims, 1 Drawing Sheet

PROCESS FOR THE PRODUCTION OF ENANTIOMERICALLY PURE OR OPTICALLY ENRICHED SERTRALINE-TETRALONE USING CONTINUOUS CHROMATOGRAPHY

This is the U.S. national stage application of PCT/US99/09037, filed Apr. 27, 1999, now WO 99/57089 published Nov. 11, 1999.

BACKGROUND OF THE INVENTION

This invention relates to the process for the production of enantiomerically pure or optically enriched sertraline-tetralone from a mixture containing two enantioners using continous chromatography or single column high performance chromatography. Some examples of continuous chromatography are liquid chromatography technologies know by the names cyclojet, and simulated moving bed chromatography (SMB). The concept of SMB was described in the late 1950's (U.S. Pat. Nos. 2,957,927 and 2,985,589) and has long been used in the petrochemical and sugar industries, Nicoud, R. M., LC-GC Intl. 5 (5), 43 (1992). Further reference can be made to U.S. Pat. Nos. 3,205,166; 3,291,726; and 3,310,486. A high efficiency continuous separation process using SMB is disclosed in U.S. Pat. Nos. 4,402,832; 5,518,625; 5,434,298: 5,434,299; 5,498,752; and Re 35,919 which are all incorporated by reference. In addition, "Chiral Discrimination on Polysacchride Derivatives", Yashima and Okamoto, Bull. Chem. Soc. Jpn., 68, 3289–3307(1995) discusses separation characteristics useful in chiral chromatography phases. Further discussion by Okamoto et. al. are included in The Journal of Chromatography, Part A, Volume 694, pp 101–109 (1995).

Sertraline-tetralone is the starting raw material In the synthesis of Zoloft (sertraline hydrochloride), a drug currently marketed for the treatment of depression as disclosed in U.S. Pat. Nos. 4,536,518; 5,196,607; 5,442,116; and 4,777,288, all incorporated by reference. Current processes for preparing this compound as described in the above patents resolve the racemic mixture at a late stage. This late stage resolution requires the undesired enantiomer to be carried through several steps. A significant benefit is obtained if an enantiomerically pure sertaline-tetralone is used as the starting material.

SMB combines the high resolution power of high performance liquid chromatography (HPLC) with the lower costs of classical separation processes such as crystallization. The costs of the SMB process can be reduced even further, if it is combined with a racemizatlon step converting the Inactive enantiomer Into the racemic form which could then be recycled back Into the process.

SUMMARY OF THE INVENTION

A process for chromatographically resolving an enantiomerically pure or optically enriched sertraline-tetralone from a mixture containing two enantiomers uses continuous chromatography or single column high performance chromatography. The continuous chromatography comprses a liquid mobile phase comprising at least one polar solvent and a solid chiral stationary phase comprising a derivatized polysaccharide that is selected from the amylosic, cellulosic, chitosan, xylan, curdlan, dextran and inulan class of polysaccharides. Some examples of the continuous chromatography methods are the cyclojet process or simulated moving bed chromatography process. The simulated moving bed chromatography process is preferred. The process uses a chiral stationary phase which is a member of the amylosic or cellulosic class of polysaccharides selected from cellulose tribenzoate, cellulose tricinnamate, amylose tricinnamate, amylose tris[(S)α-methyl benzyl carbamate], amylose 3,4-substituted phenyl carbamate and amylose 4-substituted phenyl-carbamate. Preferably the chiral stationary phase is an analog of amylose (3,4-substituent phenyl carbamate) wherein the subsfituent is selected from 3-chloro-4-methyl, 3-methyl-4-chloro or 3-fluoro-4-methyl. The chiral stationary phase can also preferably be a cellulose tricinnamate polysaccharide analog. The mobile phase comprises a solvent that is selected from heptane, hexane, isopropyl, ethanol, methanol. methyl acetate, acetonitrile, methyleno chloride, ethyl acetate and/or mixtures thereof. Preferably the mobile phase is selected from acetonitrile and/or a mixture of acetonitrile and methanol or ethanol and/or a mixture of ethanol and ethyl acetate. In one embodiment the chiral stationary phase is cellulose tricinnamate with a mobile phase of ethanol/ethyl acetate wherein the percentage of ethanol in the mobile phase mixture is greater than 50%. Preferably the chiral stationary phase is amylose (3-chloro-4-methylphenyl carbamate) and the mobile phase is acetonitrile/methanol wherein the percentage of acetonitrile in the mobile phase mixture is greater than 50%. The chromatographic retention times are increased or decreased by varying the mobile phase components. The separation affords at least one of the enantiomers a recovery of greater than or equal to 90 percent. The temperature range is about 5 to 45° C., preferably 20 to 40° C. The separation factor α is about 1.2 to 5.0. Using a temperature of about 40° C. takes advantage of an increased solubility of sertratine tetralone in the mobile phase. The chiral stationary phase polysaccharide derivative can also be immobilized on silica gel, zirconium, alumina, ceramics and other silicas.

DESCRIPTION OF THE INVENTION

The process of the invention can be applied to any continuous chromatographic method capable of separating the chiral tetralone. One example is the cycloject method described in U.S. Pat. No. 5,630,943. Another continuous chromatographic method of separating the chiral totralone is by Simulated Moving Bed Chromatography as described In U.S. Pat. Nos. 5,470,464; 5,705,061; 5,422,077; 5,456,825 and EPO 586,385.

The Simulated Moving Bed (SMB) Chromatography for the production of enantiomerically pure or optically enriched sertraline-tetralone from a mixture containing two enantiomers is described below. The punrication is achieved using SMB comprising a set of columns packed with a chromatographic chiral stationary phase [CSP] capable of chiral recognition; ports for the continuous introduction of solvent desorbent (mobile phase) and feed; ports for the continuous removal of raffinate (solution containing the less strongly retained enantiomer) and extract (solution containing the more strongly retained enantiomer); and a means of recycling fluid through the system, if necessary. The columns are connected such that the outlet of each column is connected to the inlet of the next column also with the outlet of the last column being connected to the inlet of the first column.

Examples of suitable CSP and mobile phases for the sotraline tetralone are shown in the Table 1 below.

TABLE 1

| CLASS | SPECIFIC CHIRAL SELECTOR | MOBILE PHASE | TEMP °C. | UV wavelength (nm) | α |
|---|---|---|---|---|---|
| Cellulose esters | Cellulose tribenzoate | Hexane/Isopropanol (96/4 v/v) | 40 | 280 | 1.65 |
| Cellulose esters | Cellulose tricinnamate | Ethanol/Ethyl Acetate (85/15 v/v) | 25 | 280 | 1.33 |
| Amylose esters | Amylose tricinnamate | Ethanol/Methyl Acetate (80/20 v/v) | 20 | 230 | 1.5 |
| Amylose aralkycarbamate | Amylose tris[(S)-α-methylbenzyl carbamate] | Hexane/Isopropanol (69/4 v/v) | 25 | 254 | 1.34 |
| Amylose phenylcarbamates | Amylose 3,4-substituted phenylcarbamate derivative | 1. Acetonitrile/Methanol (90/10 v/v) 2. acetonitrile 3. acetonitrile/alcohol mixtures | 25–40 | 230 at 25° C. | 2.13 at 25° C. |
| Amylose phenylcarbamates | Amylose 4-substituted phenylcarbamate derivative | Heptane/Isopropanol 96/4 v/v) | 25 | 280 | 1.45 |

The UV Wavelength represents the dectector wavelength used to monitor the elution of the two enantiomers. α represents the separation factor for the sertraline tetralone separation single column which is 4.6 mm ID×250 mm.

General Procedure For Experimental Examples

Figure 1:
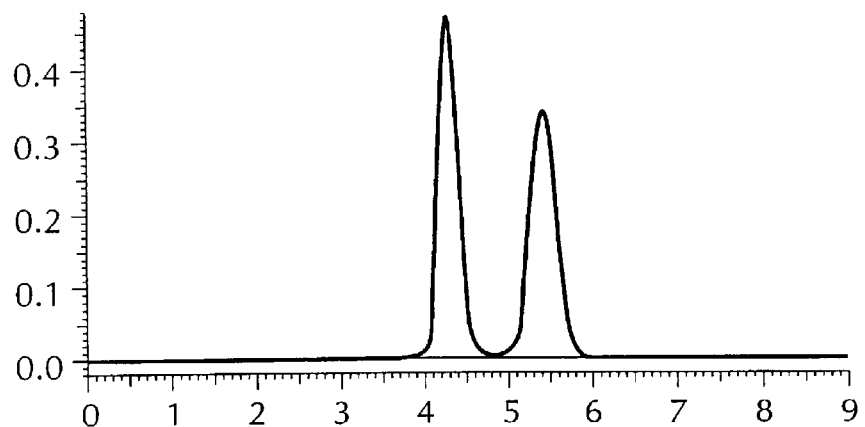
FIG. 1 shows an analytical chromatogram of the sertraline-tetralone enantiomers in which the separation factor α is between 1 and 2.

Separation on a SMB system was examined on a CSP column. In this example, the enantiomer of interest was less retained and would be recovered in the raffinate stream. This separation was used to optimize the SMB parameters and is shown in FIG. 1. In FIG. 1. The X-axis denotes the retention time in minutes and the Y-axis denotes the concentration of the component. The analytical chromatogram shows that the separation is difficult, having a separation factor α [described above] of between 1.2<α<5. The experimental conditions were as follows: chiral stationary phase: CSP 20 μm, eluent and derivatives thereof: acetonitrile/methanol 90/10 (v/v), column: 25 cm length, 0.46 cm I.D., temperature: 25° C., feed concentration: 1 g/l—Volume injected: 20 μl—Flow-rate: 1 mm/min.

The optimization of the operating conditions of a SMB is preferably done using a simulation tool, a methodology based on the modeling/simulation of non-linear n. chromatography as described in Charton F., and Nicoud, R. M., J. Chrom, 702,97–112 (1995).

If racemization of the undesired enantiomer is considered, then the undesired isomer is chemically racemized with NaOH in acetonitrile using catalytic amounts of methanol as described herein below In Example 4. The yields after solvent evaporation were above 90%.

There are two options available if racemization is desired:
Option 1: The less retained enantiomer is mostly recovered In the raffinate and the solution to be racemlzed contains almost exclusively the more retained enantiomer.
Option 2: The less retained enantiomer is partly recovered in the ralfinate and the solution to be racemized contains a significant amount of both enantiomers.

When option 1 is chosen, the amount of sertraline-tetralone to be racemized is minimized, but when option 2 is chosen it is possible to increase the SMB throughput and consequenfly, to decrease its size.

The two options were studied first by numerical simulations which allow one to make a fast parametric study of the process. In the case of option 2, the recovery yield of the less retained enantiomer in the raffinate was an additional parameter that could be varied to achieve optimum performance. It was found that a recovery yield of above 90% leads to a good compromise between the improvement of the SMB performance and the increase of the amount of sertraline-tetralone to be racemized.

In the case of large scale enantiomeric separations by SMB, the cost of the purification is mainly linked to the productivity, the influence of the eluent consumption being secondary. Consequently, in the present case where racemization is expected to be relatively inexpensive. Option 2 would have a clear advantage in increasing the SMB throughput.

A schematic depicting the SMB purification and racemization step is shown below:

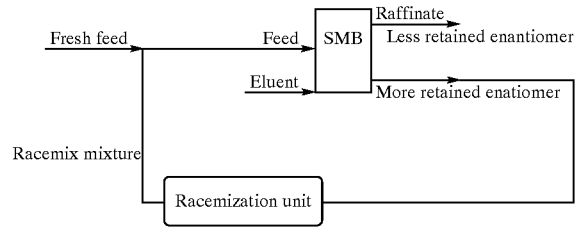

The less retained enantiomer may be recovered at the required optical purity (95–99.9%) in the raffinate stream whereas the more retained enantiomer may be collected in the extract stream. It may be possible to recycle the stream enriched in the undesired enantiomer through a racemization unit which would decrease the necessary amount of new racemic feed required.

The SMB parameters were optimized using Option 2 and the results obtained after the experimental optimization are given in the table below.

EXAMPLE 1

TABLE 2

| SMB performances at the pilot scale. | |
|---|---|
| Less retained enantiomer purity (%) | 99.2 |
| Less retained enantiomer recovery yield (%) | 91.8 |
| Calculated volume of eluent necessary (l/g enantiomer) | 0.40 |
| Productivity (kg enantiomer/year/kg Chiral Stationary Phase) | 2.88 |
| Amount of feed to be processed (g/g enantiomer recovered) | 2.18 |
| Amount of product to be racemized (g/g enantiomer recovered) | 1.18 |

Figure 2:
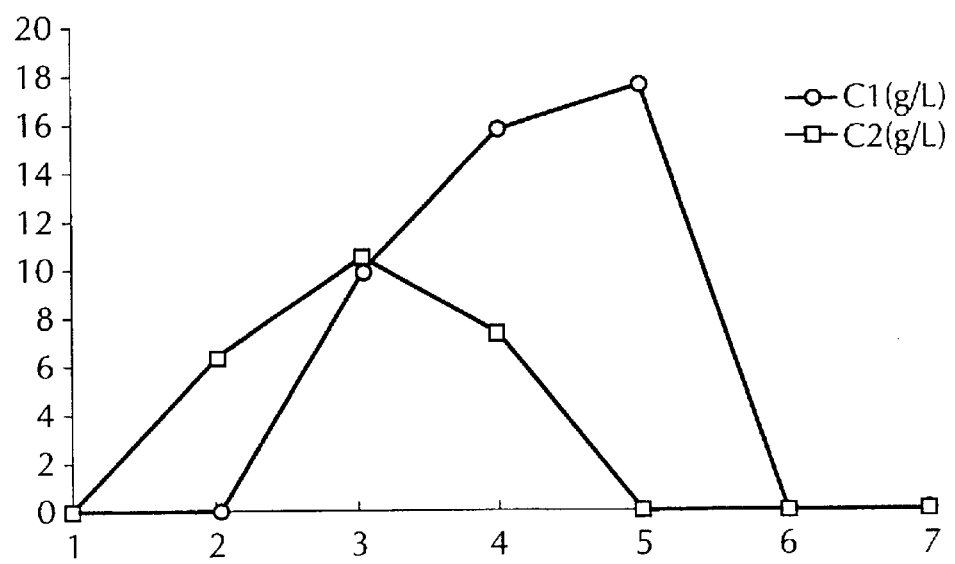
FIG. 2 shows the experimental profiles measured in the SMB at half-time period in the steady state.

The main operating parameters for the pilot scale tests are given in Table 2a below:

The experimental profiles measured in the SMB at half-time period at steady state are shown in FIG. 2. The y-axis denotes the concentration of the material in mglml and the x-axis denotes the individual columns in the SMB unit. In this figure, the feed is introduced in Column #4 (designated as #4 in FIG. 2), the eluent is introduced at Column #1 and the raffinate and extract are removed at Columns #6 and #2 respectively.

TABLE 2a

Operating parameters

| Column: (CSP) | amylose (3-chloro-4-methyl phenylcarbamate) |
|---|---|
| Mobile Phase: | acetonitrile 100% |
| Column Length: | 10.7 cm |
| Column I.D.: | 2.6 cm |
| Number of Columns: | 6 columns |
| Feed Concentration | 30 gms/liter |
| Eluent Flow-rate | 23 ml/min |
| Feed Flow Rate: | 9.3 ml/min |
| Flow Rate in Zone I: | 97.5 ml/min |
| Extract Flow Rate: | 26.1 ml/min. |
| Raffinate Flow Rate | 12.2 ml/min. |
| Period | 0.32 min |
| Temperature | 25° C. |
| Operating pressure | 25 bars |

EXAMPLE 2

TABLE 3

SMB performances at the pilot scale

| Less retained enantiomer purity (%) | 98.2 |
|---|---|
| Less retained enantiomer recovery yield (%) | 82 |
| Calculated volume of eluent necessary (liter/gm enantiomer) | 1.25 |
| Productivity (kg enantiomer per year per Kg CSP) | 56 |
| Amount of feed to be processed (Kg per Kg enantiomer recovered) | 2.44 |
| Amount of product to be racemized (Kg per Kg enantiomer recovered) | 1.44 |

The main operating parameters for the pilot scale tests are given in Table 3a below:

TABLE 3a

Operating parameters

| Type of Chiral Column: | Cellulose tricinnamate |
|---|---|
| Mobile Phase: | 85/15 v/v ethanol/ethyl acetate |
| # Columns | 6 |
| Column Length: | 10 cm |
| Column I.D.: | 2.6 cm |
| Feed Concentration (glitter) | 20 |
| Feed Flow Rate: (ml/min) | 2.85 |
| Eluent Flow-rate (ml/min) | 26.3 |
| Flow Rate in Zone I | 65 ml/min |
| Extract Flow Rate: (ml/min) | 22.9 |
| Raffinate flow rate (ml/min) | 6.3 |
| Period | 1.65 |
| Temperature | 25 |
| Pressure (bar) | 40 |

EXAMPLE 3

TABLE 4

SMB performances at the pilot scale.

| Less retained enantiomer purity (%) | 99.7 |
|---|---|
| Less retained enantiomer recovery yield (%) | 98.4 |
| Calculated volume of eluent necessary (liter/gm enantiomer) | 0.4 |

TABLE 4-continued

SMB performances at the pilot scale.

| Productivity (kg enantiomer per year per Kg CSP) | 371 |
|---|---|
| Amount of feed to be processed (Kg per Kg enantiomer recovered) | 2.03 |
| Amount of product to be racemized (kg per Kg enantiomer recovered) | 1.03 |

The main operating parameters for the pilot scale tests are given in Table 4a below:

TABLE 4a

Operating parameters

| Type of Chiral Column: | Amylose (3-chloro-4-methylphenyl carbamate) |
|---|---|
| Mobile Phase: | 90/10 v/v acetonitrile/MeOH |
| # Columns | 6 |
| Column Length | 9.9 cm |
| Column I.D.: | 4.8 cm |
| Feed Concentration (glitter) | 30 |
| Feed Flow Rate: (ml/min) | 37 |
| Eluent Flow Rate (ml/min) | 186 |
| Flow Rate in Zone 1 | 388 ml/min |
| Extract Flow Rate: (ml/min) | 147 |
| Raffinate flow rate (ml/min) | 76 |
| Temperature | 25 |
| Pressure (bar) | 25 |

As seen from Example 2 in Table 3 and Example 3 in Table 4 there is a 7.39 fold increase in productivity by changing the CSP and the mobile phase.

A chemical racemization process for the tetralone is given in Example 4 below.

EXAMPLE 4

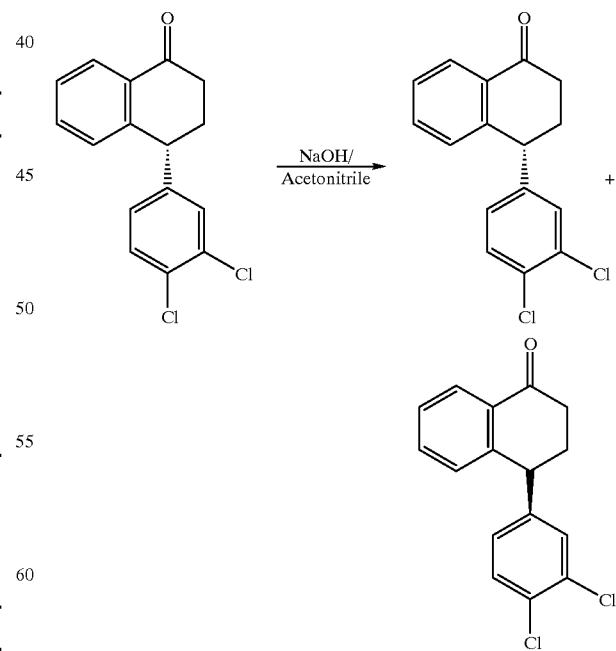

In a nitrogen purged reaction vessel equipped with a mechanical stirrer lubricated with mineral oil with a bubbler nitrogen inlet and a reflux condenser, 100 grams of (−)totralone, 1000.00 ml of acetonitrile, 0.8 grams sodium hydroxide pellets and 0.5 ml of methanol were combined. The resulting slurry was heated to 50° C. and stirred at this temperature for 6 hrs. The reaction was monitored by chiral HPLC until complete racemization was achieved. The reaction mixture was diluted with 2000 ml of acetonitrile and the pH was adjusted to 6–8 using methanolic HCl. The mothanolic HCl is made by charging 100 grams of methanol in a separate round bottom flask and cooling the methanol to 0° C. and then adding 15 grams of HCl. The reaction mixture was agigtated for 30 minutes and the resulting NaCl salts were filtered using a filter acid. Using a rotovap the solvent was evaporated to afford 97% of racemic totralone.

It should be understood that the invention is not limited to the particular embodiments described herein, but that various changes and modification may be made without departing from the spirit and scope of this novel concept as defined by the following claims.

What is claimed is:

1. A process for chromatographically resolving enantiomerically pure or optically enriched sertraline-tetralone from a mixture containing two enantiomers using continuous chromatography, the continuous chromatography comprising a liquid mobile phase comprising a least one polar solvent and a solid chiral stationary phase comprising a derivatized polysaccharide that is selected from the amylosic, cellulosic, chitosan, xylan, curdlan, dextran, and inulan class of polysaccharides.

2. A method according to claim 1 wherein the chromatographic method employed is a cyclojet process.

3. A process for chromatographically resolving enantiomerically pure or optically enriched sertraline tetralone from a mixture containing two enantiomers using single column high performance chromatography comprising a liquid mobile phase comprising at least one polar solvent and a solid chiral phase comprising a derivatized polysaccharide that is selected from the amylosic, cellulosic, chitosan, xylan, curdlan, dextran and inulan class of polysaccharides.

4. A process for the production of enantiomerically pure or optically enriched sertraline-tetralone from a mixture containing tyro enanflomers using simulated moving bed chromatography, the moving bed chromatography comprising a liquid mobile phase comprising a least one polar solvent and a solid chiral stationary phase comprising a derivatized polysaccharide that is selected from the amylosic, cellulosic, chitosan, xylan, curdlan, dextran, and inulan class of polysaccharides.

5. The process of claim 4 wherein the chiral stationary phase is a member of the amylosic or cellulosic class of polysaccharides that is selected from cellulose tribenzoate cellulose tricinnamate, amylose tricinnamate, amylose tris [(S)α-methyl benzyl carbamate] amylose 3,4-substituted phenyl carbamatc and amylose 4-substituted phenylcarbamate.

6. The process of claim 5 wherein the chiral stationary phase is an analog of amylose (3,4 substituted phenyl carbamate) wherein the substitutent is selected from 3-chloro-4-methyl, 3-methyl-4-chloro, or 3-fluoro-4-methyl.

7. The process of claim 5 wherein the chiral stationary phase is a cellulose tricinnaimate polysaccharide analog.

8. The process of claim 4 wherein the mobile phase comprises a solvent that is selected from heptane, hexane, isopropanol, ethanol, methanol, methyl acetate, acetonitrile, methylene chloride, ethyl acetate and/or mixtures thereof.

9. The process of claim 8, wherein the mobile phase is selected from acetonitrile and/or a mixture of acetonitrite and methanol or ethanol and/or a mixture of ethylacetate and ethanol.

10. The process of claim 4, wherein the polysaccharide derivative is immoblized on silica gel, zirconium, alumina, ceramics and other silicas.

11. The process of claim 4, using an amylose 3,4-substituted phenyl carbamate derivative polysaccharide analog with a mobile phase of acetonitrile and/or a mixture of acetonitrile and methanol.

12. The process of claim 11, using a an amylose (3-Chloro-4-methyl-phenyl carbamate) with a mobile phase of acetonitriletmethanol wherein the percentage of acetonitrile in the mobile phase mixture is greater than 50 percent (v/v).

13. The process or claim 4, using cellulose tricinnamate with a mobile phase of ethanol/othyl acetate wherein the percentage of ethanol in the mobile phase mixture, is greater than 50% (v/v).

14. The process of claim 4, wherein retention times are increased or decreased by varying the mobile phase components.

15. The process of claim 4, wherein said separation affords at least one of the enantiomers a recovery of greater than or equal to 90%.

16. The process of claim 4, using a temperature range of about 5 to 45° C.

17. The process of claim 16, using a temperature range of about 20 to 40° C.

18. The process of claim 4, wherein the separation factor α is about 1.2 to 5.0.

19. The process of claim 17 using a temperature of about 40° C.

20. A process for resolving enantiomerically pure or optically enriched sertraline-tetralone from a mixture containing two enantiomers using chromatography comprising using a mobile phase comprising said mixture and at least one polar solvent and a solid chiral stationary phase comprising a derivatized polysaccharide immobilized on a substrate wherein said derivatized polysaccharide is selected from the group consisting of amylosic, cellulosic, chitosan, xylan, curdlan, dextran and inulan class polysaccharides.

21. A process for resolving enantiomerically pure or optically enriched sertraline-tetralone from a mixture containing two enantiomers using chromatography comprising using a mobile phase comprising said mixture and at least one polar solvent and a solid chiral stationary phase comprising a derivatized polysaccharide immobilized on a substrate wherein said derivatized polysaccharide is selected from the group consisting of amylosic, cellulosic, chitosan, xylan, curdlan, and inulan class polysacchlarides.

\* \* \* \* \*

UNITED STATES PATENT AND TRADEMARK OFFICE
CERTIFICATE OF CORRECTION

PATENT NO.     : 6,444,854 B1
DATED          : September 3, 2002
INVENTOR(S)    : Oliver Dapremont et al.

It is certified that error appears in the above-identified patent and that said Letters Patent is hereby corrected as shown below:

Title page,
Insert -- Related U.S. Application Data [60] Provisional application No. 60/083,851 filed on May 1, 1998. --.

Column 1,
Line 9, after "1999" insert -- , which application claims the benefit of U.S. Provisional Application No. 60/083,851 filed May 1, 1998. --.

Signed and Sealed this

Twenty-fourth Day of December, 2002

JAMES E. ROGAN
*Director of the United States Patent and Trademark Office*